(12) United States Patent
Joo et al.

(10) Patent No.: US 10,385,011 B2
(45) Date of Patent: Aug. 20, 2019

(54) BENZOIC ACID AMIDE COMPOUND

(71) Applicant: AMOREPACIFIC CORPORATION, Seoul (KR)

(72) Inventors: Yung Hyup Joo, Yongin-si (KR); Soo Jeong Choi, Yongin-si (KR); Heung Soo Baek, Yongin-si (KR); Chang Seok Lee, Yongin-si (KR); Jeong Hwan Kim, Yongin-si (KR); Yongjin Kim, Yongin-si (KR); Hong-Ju Shin, Yongin-si (KR); Ho Sik Rho, Yongin-si (KR); Song Seok Shin, Yongin-si (KR); Jon Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/561,585

(22) PCT Filed: Mar. 30, 2016

(86) PCT No.: PCT/KR2016/003235
§ 371 (c)(1),
(2) Date: Sep. 26, 2017

(87) PCT Pub. No.: WO2016/159644
PCT Pub. Date: Oct. 6, 2016

(65) Prior Publication Data
US 2018/0065922 A1    Mar. 8, 2018

(30) Foreign Application Priority Data

Mar. 31, 2015  (KR) ........................ 10-2015-0045201

(51) Int. Cl.
| | |
|---|---|
| *A61K 31/16* | (2006.01) |
| *C07C 231/12* | (2006.01) |
| *C07C 233/70* | (2006.01) |
| *A61K 8/42* | (2006.01) |
| *A61K 31/166* | (2006.01) |
| *A61Q 19/02* | (2006.01) |
| *A23L 29/00* | (2016.01) |
| *C07C 235/48* | (2006.01) |

(52) U.S. Cl.
CPC ............ *C07C 233/70* (2013.01); *A23L 29/00* (2016.08); *A61K 8/42* (2013.01); *A61K 31/166* (2013.01); *A61Q 19/02* (2013.01); *C07C 231/12* (2013.01); *C07C 235/48* (2013.01)

(58) Field of Classification Search
CPC .............................. C07C 231/12; A61K 31/166
USPC ......................................................... 564/123
See application file for complete search history.

(56) References Cited

U.S. PATENT DOCUMENTS

| | | | |
|---|---|---|---|
| 2008/0214675 A1 | 9/2008 | Ley et al. | |
| 2008/0280989 A1 | 11/2008 | Kim et al. | |
| 2014/0234241 A1 | 8/2014 | Joo et al. | |

FOREIGN PATENT DOCUMENTS

| | | |
|---|---|---|
| EP | 1 430 016 B1 | 12/2008 |
| JP | 8-143525 A | 6/1996 |
| KR | 10-2002-0049340 A | 6/2002 |
| KR | 10-2003-0026062 A | 3/2003 |
| KR | 10-2004-0092539 A | 11/2004 |
| KR | 10-0680584 B1 | 2/2007 |
| KR | 10-2007-0046577 A | 5/2007 |
| KR | 10-2013-0015954 A | 2/2013 |

OTHER PUBLICATIONS

Heung Soo Baek et al., "Adamantyl N-benzylbenzamide: New series of depigmentation agents with tyrosinase inhibitory activity", Bioorganic & Medicinal Chemistry Letters, vol. 22, No. 5, 2011, pp. 2110-2113.
Jae Won Yoo et al., "Substituted N-Benzylbenzamide: A New Series of Depigmentation Agents with Tyrosinase Inhibitory Activity", Bull. Korean Chem. Soc., vol. 37, No. 10, 2016, pp. 1736-1739.
Extended European Search Report from European Application No. 16773425.0, dated Sep. 14, 2018.
International Search Report for PCT/KR2016/003235 (dated Jul. 1, 2016).
Written Opinion for PCT/KR2016/003235 (dated Jul. 1, 2016).

*Primary Examiner* — Ana Z Muresan
(74) *Attorney, Agent, or Firm* — Merchant & Gould P.C.

(57) ABSTRACT

Disclosed are a novel benzoic acid amide derivative compound, an isomer thereof, a pharmaceutically acceptable salt thereof, a prodrug thereof, a hydrate thereof, or a solvate thereof. The novel compound and the like inhibit melanin production, prevent tyrosinase activity, and have an excellent skin whitening effect.

14 Claims, No Drawings

BENZOIC ACID AMIDE COMPOUND

This application is a U.S. National Stage Application under 35 U.S.C. § 371 of International Patent Application No. PCT/KR2016/003235 filed Mar. 30, 2016, which claims the benefit of priority to Korean Patent Application No. 10-2015-0045201 filed Mar. 31, 2015 and all the benefits accruing therefrom under 35 U.S.C. § 119, the contents of all of which are hereby incorporated by reference in their entireties. The International Application was published in Korean on Oct. 6, 2016 as WO 2016/159644.

TECHNICAL FIELD

The present disclosure relates to a novel benzoic acid amide compound and a use thereof.

BACKGROUND ART

Melanin blocks UV at the epidermis to protect skin organs beneath the dermis and scavenges free radicals to protect the skin. Also, melanin is the primary determinant of skin color and thus is the cause of pigmentation such as stains, freckles and dark spots when existing in excess.

Melanin is produced on melanocytes, which are found in the basal layer of the epidermis. It is known that the production of melanin is promoted by stimuli such as UV or inflammation. Accordingly, the melanin production can be inhibited by decreasing external stimulation, blocking signal transduction, or inhibiting synthesis or activity of tyrosinase, which is a melanin-producing enzyme.

Until now, kojic acid, hydroquinone, arbutin, azelaic acid, aloesin, 4-butylresorcinol, resveratrol, ceramide, sphingosine-1-phosphate, sphingosylphosphorylcholline, and the like are known to be able to regulate melanin production by promoting tyrosinase decomposition or regulating glycosylation. However, these substances are not widely used due to unsatisfactory skin whitening effect and stability as well as skin irritation. Accordingly, it is necessary to develop a substance having excellent skin whitening effect with low side effects.

CITATION LIST

Patent Literature

[Patent Literature 1] Korean Patent Publication No.: 10-2004-0092539
[Patent Literature 2] Korean Patent Publication No.: 10-2003-0026062
[Patent Literature 3] US Patent Publication No.: 20140234241A1

SUMMARY OF INVENTION

Technical Problem

An aspect of the present invention is to provide a novel benzoic acid amide derivative compound.

Another aspect of the present invention is to provide a composition comprising a benzoic acid amide derivative compound exhibiting skin whitening effects.

Solution to Problem

An aspect of the present invention provides a compound comprising a structure of the following Chemical Formula 1, an isomer thereof, a pharmaceutically acceptable salt thereof, a prodrug thereof, a hydrate thereof, or a solvate thereof:

[Chemical Formula 1]

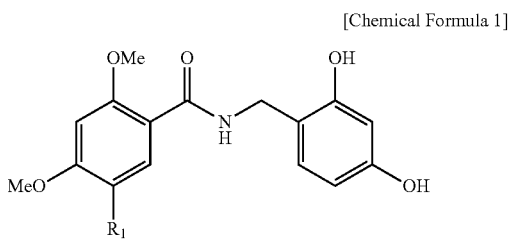

$R_1$ of Chemical Formula 1 is selected from the group consisting of halogen, $C_1$-$C_5$ alkyl, $C_3$-$C_6$ cycloalkyl, $C_3$-$C_6$ cycloalkenyl and $C_6$-$C_{18}$ aryl group, and the aryl group is unsubstituted or substituted with one or more selected from the group consisting of halogen, $C_1$-$C_5$ alkyl, $C_1$-$C_5$ alkoxy, methylenedioxy and nitro groups.

Another aspect of the present invention provides a composition for skin whitening, comprising the compound of Chemical Formula 1, an isomer thereof, a pharmaceutically acceptable salt thereof, a prodrug thereof, a hydrate thereof, or a solvate thereof.

Advantageous Effects of Invention

An aspect of the present invention provides a novel compound exhibiting skin whitening, an isomer thereof, a pharmaceutically acceptable salt thereof, a prodrug thereof, a hydrate thereof, or a solvate thereof.

Another aspect of the present invention provides a composition comprising a novel compound according to the present invention, an isomer thereof, a pharmaceutically acceptable salt thereof, a prodrug thereof, a hydrate thereof or a solvate thereof.

Still another aspect of the present invention provides an effect of inhibiting melanin production by the composition comprising a novel compound, an isomer thereof, a pharmaceutically acceptable salt thereof, a prodrug thereof, a hydrate thereof or a solvate thereof.

Yet another aspect of the present invention provides an effect of inhibiting tyrosinase activity by the composition comprising a novel compound, an isomer thereof, a pharmaceutically acceptable salt thereof, a prodrug thereof, a hydrate thereof or a solvate thereof.

Yet another aspect of the present invention provides an excellent skin whitening effect by the composition comprising a novel compound, an isomer thereof, a pharmaceutically acceptable salt thereof, a prodrug thereof, a hydrate thereof or a solvate thereof.

DESCRIPTION OF EMBODIMENTS

Definition

As used herein, "skin" refers to the tissue that covers the body surface of an animal and has the broadest concept including not only the face or body but also the scalp and hair.

As used herein, "alkyl" refers to a monovalent saturated aliphatic hydrocarbon chain. The hydrocarbon chain may be either straight or branched. In an aspect of the present invention, the "alkyl" may have 1-5 carbon atoms ("$C_1$-$C_5$ alkyl"). In another aspect, it may have 1-4 carbon atoms ("$C_1$-$C_4$ alkyl"). Specifically, the "alkyl" includes methyl, ethyl, n-propyl, isopropyl, n-butyl, isobutyl, tert-butyl or t-amyl, but is not limited thereto.

As used herein, "alkoxy" refers to an —OR group, where R is an alkyl group defined above. Specifically, the "alkoxy" includes methoxy, ethoxy, n-propoxy, isopropoxy, n-butoxy, tert-butoxy, sec-butoxy, n-pentoxy or 1,2-dimethylbutoxy, but is not limited thereto.

As used herein, "cycloalkyl" refers to a cyclic saturated aliphatic hydrocarbon group. The number following C corresponds to the number of carbon atoms that form a ring and is mentioned with a cycloalkyl group. For example, "$C_3$-$C_6$ cycloalkyl" refers to cycloalkyl having 3-6 ring-forming carbon atoms. In an aspect of the present invention, examples of the "cycloalkyl" include cyclopropyl, cyclobutyl, cyclopentyl or cyclohexyl, but are not limited thereto. In another aspect of the present invention, the "cycloalkyl" group may be substituted with one or more alkyl group, for example, with a $C_1$-$C_6$ alkyl group, specifically with a $C_1$-$C_4$ alkyl group, more specifically with a methyl group. When the "cycloalkyl" has one or more substituents, the substituents may be identical or different.

As used herein, "cycloalkoxy" refers to an —OR group, where R is a "cycloalkyl" group defined above.

As used herein, "halo" or "halogen" includes fluoro, chloro, bromo or iodo. In an aspect of the present invention, the halo group may be fluoro or chloro.

As used herein, "aryl" refers to an aromatic hydrocarbon radical. The "aryl" group may be, for example, phenyl, naphthyl, indenyl, azulenyl or thracene, preferably phenyl.

As used herein, "isomer" includes not only optical isomers (for example, essentially pure enantiomers, essentially pure diastereomers, or mixtures thereof) but also conformation isomers (i.e., isomers different only in angles of one or more chemical bonds), position isomers (especially, tautomers), or geometric isomers (for example, cis-trans isomers).

As used herein, "essentially pure" means, for example, when used in connection with enantiomers or diastereomers, that the specific compound as an example of the enantiomer or the diastereomer is present in about 90% (w/w) or more, specifically about 95% or more, more specifically about 97% or more or about 98% or more, further more specifically about 99% or more, even more specifically about 99.5% or more.

As used herein, "pharmaceutically acceptable" means approval or possibility to be approved by a government or a regulatory organization, which is equivalent thereof, or listed in the Pharmacopoeia or other generally recognized pharmacopoeia for use in animals, more specifically in humans, since significant toxic effect can be avoided when used with a common medicinal dosage.

As used herein, "pharmaceutically acceptable salt" refers to a salt according to an aspect of the present invention, which is pharmaceutically acceptable and exhibits the desired pharmacological activity of its parent compound. The salt may be (1) an acid addition salt formed from an inorganic acid such as hydrochloric acid, hydrobromic acid, sulfuric acid, nitric acid, and phosphoric acid; or an organic acid such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, or muconic acid; or (2) a salt formed as an acidic proton present in the parent compound is substituted.

As used herein, "prodrug" refers to a drug which is chemically converted so that physical and chemical properties have been changed. It does not exhibit physiological activity, but is converted to the original drug through chemical or enzymatic action in vivo after its administration, thereby exerting medicinal effects.

As used herein, "hydrate" refers to a compound bound with water. It is used in a broad concept, including an inclusion compound which lacks chemical bonding with water.

As used herein, "solvate" refers to a higher-order compound formed between a solute molecule or ion and a solvent molecule or ion.

DETAILED DESCRIPTION

In an aspect, the present invention provides a compound comprising a structure of the following Chemical Formula 1, an isomer thereof, a pharmaceutically acceptable salt thereof, a prodrug thereof, a hydrate thereof or a solvate thereof:

[Chemical Formula 1]

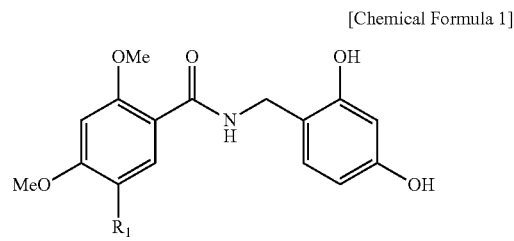

$R_1$ of Chemical Formula 1 is independently selected from the group consisting of halogen, $C_1$-$C_4$ alkyl, $C_3$-$C_6$ cycloalkyl, $C_3$-$C_6$ cycloalkenyl, and aryl group, wherein the aryl group is unsubstituted or substituted with one or more selected from the group consisting of halogen, $C_1$-$C_5$ alkyl, $C_1$-$C_5$ alkoxy, methylenedioxy, and nitro groups.

In another aspect, the present invention provides the compound, the isomer thereof, the pharmaceutically acceptable salt thereof, the prodrug thereof, the hydrate thereof, or the solvate thereof, comprising one selected from the group consisting of N-(2,4-dihydroxy-benzyl)-2,4-dimethoxy-5-methyl-benzoic acid amide, 5-bromo-N-(2,4-dihydroxybenzyl)-2,4-dimethoxy-benzoic acid amide, 5-tert-butyl-N-(2,4-dihydroxy-benzyl)-2,4-dimethoxy-benzoic acid amide, N-(2,4-dihydroxy-benzyl)-2,4-dimethoxy-5-phenyl-benzoic acid amide, N-(2,4-dihydroxy-benzyl)-2,4-dimethoxy-5-(4-fluoro-phenyl)-benzoic acid amide, N-(2,4-dihydroxy-benzyl)-2,4-dimethoxy-5-(4-methoxy-phenyl)-benzoic acid amide, 5-benzo[1,3]dioxol-5-yl-N-(2,4-dihydroxy-benzyl)-2,4-dimethoxy-benzoic acid amide, 5-cyclohexene-1-yl-N-(2,4-dihydroxy-benzyl)-2,4-dimethoxy-benzoic acid amide, N-(2,4-dihydroxy-benzyl)-2,4-dimethoxy-5-(3,5-dimethyl-phenyl)-benzoic acid amide, 5-cyclohexyl-N-(2,4-dihydroxy-benzyl)-2,4-dimethoxy-benzoic acid amide, N-(2,4-dihydroxy-benzyl)-2,4-dimethoxy-5-(3,4-difluoro-phenyl)- benzoic acid amide, and N-(2,4-dihydroxy-benzyl)-2,4-dimethoxy-5-(3-nitro-phenyl)-benzoic acid amide.

In an aspect, the present invention provides i) the first step of preparing a benzoic acid amide compound by reacting a benzoic acid derivative of the following Chemical formula 2 and a hydroxyl group substituted alkyl-phenyl amine;

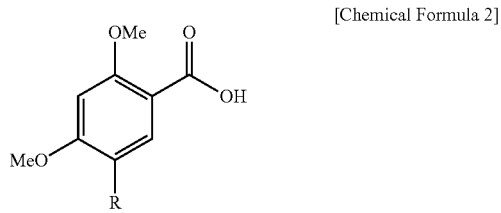

[Chemical Formula 2]

R is selected from the group consisting of halogen, $C_1$-$C_5$ alkyl, $C_3$-$C_6$ cycloalkyl, and $C_3$-$C_6$ cycloalkenyl.

In a case where the R of Chemical formula 2 is a bromine group to form a bromo benzoic acid derivative, the resulting obtained from the first step may be subject to the following second step.

In an aspect, the present invention provides the method of preparing a benzoic acid amide compound which is substituted with an alkyl or aryl group comprising the second step of reacting the resulting bromo benzoic acid amide derivative and suitable arylboronic acid under a palladium as a catalyst to form a benzoic acid amide compound with a form of bi-aryl.

In an aspect of the present disclosure, the method of preparing a benzoic acid amide compound which is substituted with an alkyl or aryl group may be schematized by the following Reaction formula 1.

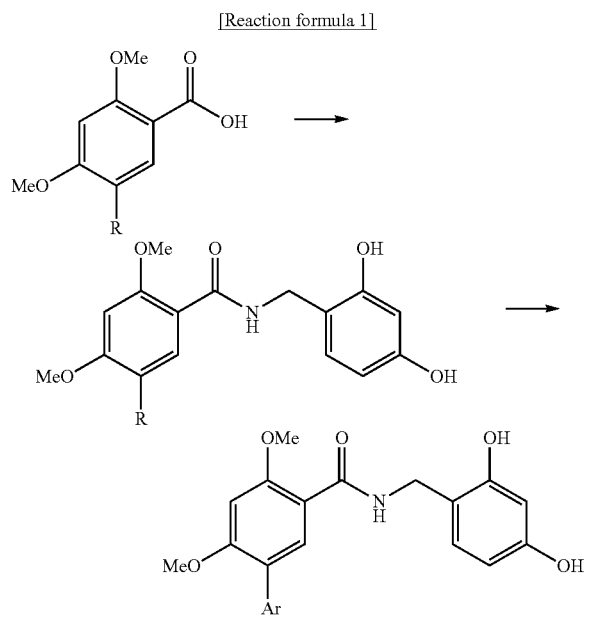

[Reaction formula 1]

In Reaction formula 1, R is selected from the group consisting of halogen, $C_1$-$C_5$ alkyl, $C_3$-$C_6$ cycloalkyl, $C_3$-$C_6$ cycloalkenyl, and aryl group, wherein the aryl group is unsubstituted or substituted with one selected from the group consisting of halogen, $C_1$-$C_5$ alkyl, $C_1$-$C_5$ alkoxy, methylenedioxy, and nitro groups. The present disclosure is selected from the group consisting of the compound including the resulting from Reaction formula 1, the isomer thereof, the pharmaceutically acceptable salt thereof, the prodrug thereof, the hydrate thereof, or the solvate thereof.

In an aspect of the present invention, a method of preparing a benzoic acid amide compound may comprise the step of preparing a benzoic acid amide compound which is substituted with alkyl or aryl group, comprising the steps of: i) preparing a benzoic acid amide compound by reacting an alkyl (or bromo) benzoic acid derivative and a hydroxyl group substituted alkyl-phenyl amine; and ii) reacting the resulting bromo benzoic acid amide derivative and suitable arylboronic acid under a palladium as a catalyst to form a benzoic acid amide compound with a form of bi-aryl.

In an aspect of the present invention, a method of preparing a benzoic acid amide compound may comprise the steps of: i) preparing a benzoic acid amide compound by reacting an alkyl (or bromo) benzoic acid derivative and a hydroxyl group substituted alkyl-phenyl amine in a presence of N-hydroxysuccinimide (HOSu) and N, N'-dicyclohexyl-carbodiimide (DCC); and ii) reacting the resulting bromo benzoic acid amide derivative and suitable arylboronic acid under a palladium as a catalyst and base condition by Suzuki cross coupling to form a benzoic acid amide compound with a form of bi-aryl.

In an aspect, the present invention provides a composition for skin whitening comprising the compound, the isomer thereof, the pharmaceutically acceptable salt thereof, the prodrug thereof, the hydrate thereof, or the solvate thereof as an active ingredient.

In an aspect, the present invention provides a method of improving skin whitening of a subject, wherein the method may comprise the step of administering an active dosage of the compound, the isomer thereof, the pharmaceutically acceptable salt thereof, the prodrug thereof, the hydrate thereof, or the solvate thereof to a subject in needed thereof.

In an aspect, the present invention provides a use of the compound, the isomer thereof, the pharmaceutically acceptable salt thereof, the prodrug thereof, the hydrate thereof, or the solvate thereof for preparing a composition for improving skin whitening.

In an aspect, the present invention provides the compound, the isomer thereof, the pharmaceutically acceptable salt thereof, the prodrug thereof, the hydrate thereof or the solvate thereof for improving skin whitening.

The compound, the isomer thereof, the pharmaceutically acceptable salt thereof, the prodrug thereof, the hydrate thereof or the solvate thereof may inhibit melanin production and prevent tyrosinase activity, thereby having excellent skin whitening effect.

In an aspect, the composition of the present invention may comprise 0.01 wt % to 20 wt % of the compound, the isomer thereof, the pharmaceutically acceptable salt thereof, the prodrug thereof, the hydrate thereof, or the solvate thereof based on total weight of the composition.

In a view, a content of the compound, the isomer thereof, the pharmaceutically acceptable salt thereof, the prodrug thereof, the hydrate thereof, or the solvate thereof may be 0.01 wt % or more, 0.02 wt % or more, 0.03 wt % or more, 0.04 wt % or more, 0.05 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1.0 wt % or more, 2.0 wt % or more, 3.0 wt % or more, 4.0 wt % or more, 4.1 wt % or more, 4.2 wt % or more, 4.3 wt % or more, 4.4 wt % or more, 4.5 wt % or more, 4.6 wt % or more, 4.7 wt % or more, 4.8 wt % or more, 4.9 wt % or more or 5.0 wt % or more based on total weight of the composition.

In a view, a content of the compound, the isomer thereof, the pharmaceutically acceptable salt thereof, the prodrug thereof, the hydrate thereof, or the solvate thereof may be 20 wt % or less, 19.5 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5.9 wt % or less, 5.8 wt % or less, 5.7 wt % or less, 5.6 wt % or less, 5.5 wt % or less, 5.4 wt % or less, 5.3 wt % or less, 5.2 wt % or less or 5.1 wt % or less based on total weight of the composition.

Within the above-described range, the effect desired by the present disclosure can be achieved adequately while satisfying both stability and safety of the composition, and the range is suitable in terms of cost effectiveness. Specifically, in the case where the compound, the isomer thereof, the pharmaceutically acceptable salt thereof, the prodrug thereof, the hydrate thereof, or the solvate thereof is included in an amount less than 0.01 wt %, skin whitening effect may be insufficient. Further, when it is included in an amount exceeding 20 wt %, cost effectiveness may wear off.

In an aspect, the present invention provides a composition for external application to skin, comprising the compound, the isomer thereof, the pharmaceutically acceptable salt thereof, the prodrug thereof, the hydrate thereof, or the solvate thereof as an active ingredient. In another aspect, the present invention provides a cosmetic composition comprising the compound, the isomer thereof, the pharmaceutically acceptable salt thereof, the prodrug thereof, the hydrate thereof, or the solvate thereof as an active ingredient. The cosmetic composition may exhibit superior skin whitening effect and, specifically, may improve or prevent stains, freckles, dark spots, or pigmentation.

The cosmetic composition according to the present invention may be provided as any formulation suitable for topical application. For example, it may be provided in the formulation of solution, oil-in-water emulsion, water-in-oil emulsion, suspension, solid, gel, powder, paste, foam, or aerosol. The composition of formulations may be prepared by a method commonly used in the art.

The cosmetic composition according to the present invention may further comprise other ingredients in a range that does not affect its primary effect negatively and preferably may provide synergic effect. Specifically, the composition according to the present invention may further comprise arbutin or ascorbic acid derivatives that can enhance skin whitening effect. Further, the cosmetic composition according to the present invention may further comprise moisturizer, emollient, surfactant, UV absorbent, antiseptic, fungicide, antioxidant, pH adjuster, organic or inorganic pigment, flavor, cooling agent, or antiperspirant. The amount of these ingredients may be determined within ranges not negatively affecting the purpose and effect of the present invention by those skilled in the art. The amount of these ingredients may be 0.01 wt % to 5 wt %, specifically 0.01 wt % to 3 wt %, based on the total weight of the composition.

In another aspect, the present invention provides a pharmaceutical composition comprising the compound, the isomer thereof, the pharmaceutically acceptable salt thereof, the prodrug thereof, the hydrate thereof, or the solvate thereof as an active ingredient. The pharmaceutical composition may exhibit excellent skin whitening effect, specifically, may improve or treat stains, freckles, dark spots, or pigmentation.

The pharmaceutical composition according to the present invention may be administered orally, parenterally, rectally, topically, transdermally, intravenously, intramuscularly, intraperitoneally, subcutaneously, or the like. Formulations for oral administration may be in the form of tablet, pill, soft or hard capsule, granule, powder, fine granule, liquid, emulsion, or pellet, but are not limited thereto. Formulations for parenteral administration may be in the form of solution, suspension, emulsion, gel, injection, medicinal drip, suppository, patch, or spray, but are not limited thereto. These formulations may be prepared easily by a method commonly used in the art and surfactant, vehicle, hydrating agent, emulsification accelerator, suspension, salt or buffer for osmotic pressure control, colorant, flavor, stabilizer, antiseptic, preservative, or other commonly used adjuvants may be used adequately.

The active ingredient of the pharmaceutical composition according to the present invention will vary depending on the age, gender, body weight, pathological condition, and severity of a subject, administration route or discretion of a diagnoser. Determination of the administration dosage considering these factors is in the level of those skilled in the art. A daily dosage may be, for example, 0.1 mg/kg/day to 100 mg/kg/day, more specifically 5 mg/kg/day to 50 mg/kg/day, but is not limited thereto.

In an aspect, the present invention provides a composition for external application to skin comprising the compound, the isomer thereof, the pharmaceutically acceptable salt thereof, the prodrug thereof, the hydrate thereof, or the solvate thereof as an active ingredient. In another aspect, the present invention provides a food composition comprising the compound, the isomer thereof, the pharmaceutically acceptable salt thereof, the prodrug thereof, the hydrate thereof, or the solvate thereof as an active ingredient. In an aspect of the present invention, the food composition may be a health functional food composition.

Formulations of the food composition according to the present invention are not particularly limited. For example, it may be formulated into a tablet, a granule, a powder, a liquid such as a drink, a caramel, a gel, a bar, and the like. The food composition of each formulation may comprise, in addition to the active ingredient, ingredients, according to the desired object, commonly used in the art that can be selected by those skilled in the art without difficulty. When applying other ingredients together, a synergic effect may be achieved.

In the food composition according to the present invention, determination of the administration dose of the active ingredient is within the level of those skilled in the art. For example, a daily dosage may be 0.1 mg/kg/day to 5000 mg/kg/day, more specifically, 1 mg/kg/day to 500 mg/kg/day. However, without being limited thereto, the administration dose may vary depending on various factors such as the age and health conditions of the subject, presence of complication(s), and the like.

For example, the food composition according to the present invention may be various foods such as a chewing gum, a caramel, a candy, a popsicle, confectionery, and the like, drinks such as a soft drink, a mineral water, an alcohol beverage, and the like, or health functional foods comprising vitamin, mineral, and the like.

In addition, the food composition according to the present invention may comprise various nutrients, vitamins, minerals (electrolytes), flavors such as synthetic and natural flavors, colorants and extenders (cheese, chocolate, and the like), pectic acid and salts thereof, alginic acid and salts thereof, organic acids, protective colloidal thickeners, pH control agents, stabilizers, preservatives, glycerin, alcohols, carbonating agents used in carbonated drinks, and the like. Further, the functional food composition of the present invention may comprise pulps used to prepare natural fruit juice, fruit juice drinks, and vegetable drinks. These ingredients may be used independently or in combination. The content of these additives is of no great importance. Usually, they are comprised within a range of about 0 parts by weight to 20 parts by weight based on 100 parts by weight of the composition of the present invention.

EXAMPLES

Hereinafter, the present invention will be described in detail through examples and experimental examples. However, the following examples and experimental examples are for illustrative purposes only and the scope of the present invention is not limited by the examples and experimental examples.

[Example 1] Preparation of 5-tert-butyl-N-(2,4-dihydroxy-benzyl)-2,4-dimethoxy-benzoic Acid Amide

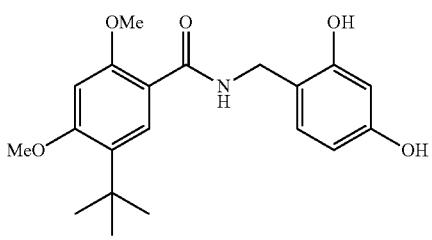 [SMILES: COc1cc(OC)c(C(C)(C)C)cc1C(=O)NCc1ccc(O)cc1O]

5-tert-butyl-2,4-dimethoxy-benzoic acid (0.5 g, 2.1 mmol) was dissolved in dichloromethane (20 mL). 2,4-dihydroxy-benzyl-amine acetate (0.46 g, 1.1 equivalent weight), HATU (=1-[Bis(dimethylamino)methylene]-1H-1,2,3-triazolo[4,5-b]pyridinium 3-oxid hexafluorophosphate, 0.95 g, 1.2 equivalent weight) and DIPEA (=N,N-Diisopropylethylamine, 0.73 ml, 2 equivalent weight) were added and stirred at room temperature for 12 hours. After completion of the reaction, the mixture was diluted with water (20 ml). After the organic layer was washed with the diluted hydrochloric acid solution, sodium bicarbonate solution and saturated aqueous sodium chloride solution, the mixture was dried by anhydrous magnesium sulfate. Then, the mixture was filtered and concentrated under reduced pressure. The residue was separated using column chromatography to obtain the desired product (0.49 g) as a white solid.

NMR results were confirmed as below. From the confirmation results as below, the white solid was confirmed as 5-tert-butyl-N-(2,4-dihydroxy-benzyl)-2,4-dimethoxy benzoic acid amide.

$^1$H NMR (300 MHz, CDCl$_3$) 8.52 (brs, NH), 8.11 (s, 1H), 7.28 (s, 1H), 7.00 (d, J=8.1 Hz, 1H), 6.40 (d, J=8.4 Hz, 1H), 6.32 (dd, J=8.1 Hz, J=2.4 Hz, 1H), 4.43 (d, J=6.6 Hz, 2H), 3.95 (s, 3H), 3.89 (s, 3H), 1.34 (s, 9H).

[Example 2] Preparation of N-(2,4-dihydroxy-benzyl)-2,4-dimethoxy-5-methyl-benzoic Acid Amide

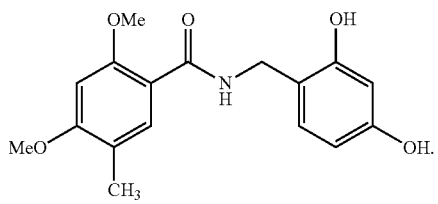 [SMILES: COc1cc(OC)c(C(=O)NCc2ccc(O)cc2O)cc1C]

A method which was substantially same method used in example 1 was used except for using 5-methyl-2,4-dimethoxy-benzoic acid (0.4 g, 2.04 mmol) instead of 5-tert-butyl-2,4-dimethoxy-benzoic acid (2.1 mmol) and using 2,4-dihydroxy-benzylamine hydrochloride (0.39 g, 1.1 eq.) instead of 2,4-hydroxy benzylamine acetate (0.46 g, 1.1 eq.) so that the desired product was obtained as a white solid (0.48 g).

NMR results were confirmed as below. From the confirmation results as below, the white solid was confirmed as N-(2,4-dihydroxy-benzyl)-2,4-dimethoxy-5-methyl-benzoic acid amide.

$^1$H NMR (300 MHz, DMSO-d$_6$) 9.51 (s, OH), 8.57 (bs, NH), 7.69 (s, 1H), 6.90 (d, J=8.1 Hz, 1H), 6.65 (s, 1H), 6.27 (s, 1H), 6.12 (d, J=8.4 Hz, 1H), 4.29 (d, J=5.4 Hz, 2H), 3.92 (s, 3H), 3.86 (s, 3H) and 2.08 (s, 3H).

[Example 3] Preparation of 5-bromo-N-(2,4-dihydroxy-benzyl)-2,4-dimethoxy-benzoic Acid Amide

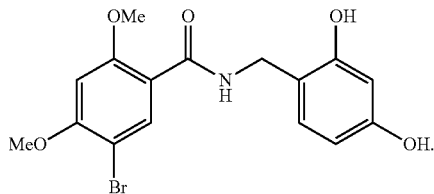 [SMILES: COc1cc(OC)c(C(=O)NCc2ccc(O)cc2O)cc1Br]

A method which was substantially same method used in Example 1 was used except for using 5-bromo-2,4-dimethoxy-benzoic acid (4 g, 15.3 mmol) instead of 5-tert-butyl-2,4-dimethoxy-benzoic acid (2.1 mmol) and using 2,4-dihydroxy-benzylamine hydrochloride (3.36 g, 1.1 eq.) instead of 2,4-hydroxy benzylamine acetate (0.46 g, 1.1 eq.) so that the desired product was obtained as a white solid (4.68 g).

NMR results were confirmed as below. From the confirmation results as below, the white solid was confirmed as 5-bromo-N-(2,4-dihydroxy-benzyl)-2,4-dimethoxy-benzoic acid amide.

$^1$H NMR (300 MHz, DMSO-d$_6$) 9.59 (s, OH), 9.14 (s, OH), 8.53 (bs, NH), 8.00 (s, 1H), 6.92 (d, J=8.1 Hz, 1H), 6.81 (s, 1H), 6.28 (s, 1H), 6.15 (d, J=8.1 Hz, 1H), 4.31 (d, J=5.4 Hz, 2H), 3.97 (s, 3H), 3.94 (s, 3H).

[Example 4] Preparation of N-(2,4-dihydroxy-benzyl)-2,4-dimethoxy-5-phenyl-benzoic Acid Amide A method which was substantially same method used in Example 1 was used except for using 4,6-dimethoxy-biphenyl-3-carboxylic acid (0.05 g, 0.19 mmol) instead of 5-tertbutyl-2,4-dimethoxy-benzoic acid (2.1 mmol) so that the desired product was obtained as a white solid (0.053 g).

NMR results were confirmed as below. From the confirmation results as below, the white solid was confirmed as N-(2,4-dihydroxy-benzyl)-2,4-dimethoxy-5-phenyl-benzoic acid amide.

$^1$H NMR (300 MHz, DMSO-$d_6$) 9.66 (s, OH), 9.15 (s, OH), 8.59 (bs, NH), 7.84 (s, 1H), 7.40 (m, 4H), 7.32 (m, 1H), 6.95 (d, J=8.1 Hz, 1H), 6.81 (s, 1H), 6.30 (s, 1H), 6.17 (dd, J=8.1 Hz, J=1.8 Hz, 1H), 4.33 (d, J=5.4 Hz, 2H), 4.01 (s, 3H), 3.87 (s, 3H).

[Example 5] Preparation of N-(2,4-dihydroxy-benzyl)-2,4-dimethoxy-5-(4-methoxy-phenyl) Benzoic Acid Amide

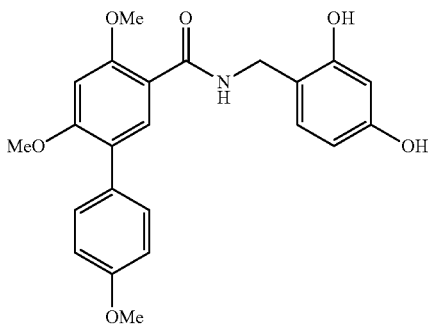 [SMILES: COc1cc(OC)c(-c2ccc(F)cc2)cc1C(=O)NCc1ccc(O)cc1O]

5-bromo-N-(2,4-dihydroxy-benzyl)-2,4-dimethoxy-benzoic acid amide (0.42 g, 1.1 mmol) obtained in Example 3 and 4-methoxy benzene boronic acid (0.2 g, 1.3 mmol) were dissolved in toluene (20 ml) and ethanol (20 ml). 2 M sodium carbonate solution (2 ml) was added to the solution. Then tetrakis (triphenylphosphine)-palladium (0) (0.04 g, 3 mol %) was added as a catalyst. The mixture was refluxed at 100° C. for 6 hours. After completion of the reaction, the mixture was diluted with water and then was extracted with dichloromethane. Then the organic layer was dried under anhydrous magnesium sulfate to be concentrated under reduced pressure. The residue was separated using column chromatography to obtain the desired product (0.1 g) as a white solid.

NMR results were confirmed as below. From the confirmation results as below, the white solid was confirmed as N-(2,4-dihydroxy-benzyl)-2,4-dimethoxy-5-(4-methoxy-phenyl) benzoic acid amide.

$^1$H NMR (300 MHz, DMSO-$d_6$) 9.68 (s, OH), 9.17 (s, OH), 8.59 (brs, NH), 7.81 (s, 1H), 7.36-7.34 (m, 2H), 6.90-6.93 (m, 3H), 6.79 (s, 1H), 6.28 (s, 1H), 6.18-6.15 (m, 1H), 4.33-4.31 (m, 2H), 3.99 (s, 3H), 3.86 (s, 3H), 3.77 (s, 3H).

[Example 6] Preparation of N-(2,4-dihydroxy-benzyl)-2,4-dimethoxy-5-(4-fluoro-phenyl)-benzoic Acid Amide

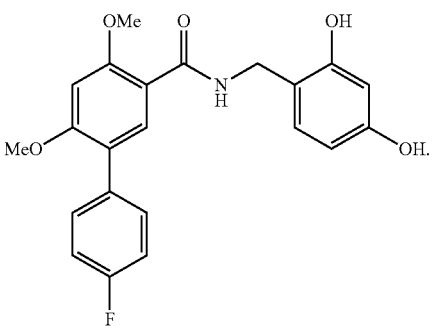

A method which was substantially same method used in Example 5 was used except for using 4-fluorobenzene boronic acid (0.18 g) instead of 4-methoxy-benzene boronic acid (0.2 g, 1.3 mmol) so that the desired product was obtained as a white solid (0.1 g).

NMR results were confirmed as below. From the confirmation results as below, the white solid was confirmed as N-(2,4-dihydroxy-benzyl)-2,4-dimethoxy-5-(4-fluoro-phenyl)-benzoic acid amide.

$^1$H NMR (300 MHz, DMSO-$d_6$) 9.65 (s, 1H), 9.14 (s, 1H), 8.58 (brs, 1H), 7.82 (m, 1H), 7.46-7.44 (m, 2H), 7.23-7.19 (m, 2H), 6.95-6.93 (m, 1H), 6.82 (s, 1H), 6.28 (s, 1H), 6.18-6.15 (m, 1H), 4.31 (m, 2H), 4.01 (s, 3H), 3.88 (s, 3H).

[Example 7] Preparation of 5-benzo[1,3]dioxol-5-yl-N-(2,4-dihydroxy-benzyl)-2,4-dimethoxy-benzoic Acid Amide

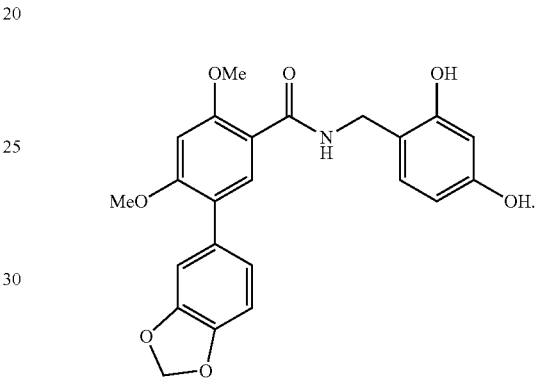

A method which was substantially same method used in Example 5 was used except for using 3,4(-methylenedioxy) phenyl boronic acid (0.22 g) instead of 4-methoxy-benzene boronic acid (0.2 g, 1.3 mmol) so that the desired product was obtained as a white solid (0.11 g).

NMR results were confirmed as below. From the confirmation results as below, the white solid was confirmed as 5-benzo[1,3]dioxol-5-yl-N-(2,4-dihydroxy-benzyl)-2,4-dimethoxy-benzoic acid amide.

$^1$H NMR (300 MHz, DMSO-$d_6$) 9.64 (s, 1H), 9.14 (s, 1H), 8.58-8.54 (m, 1H), 7.79 (s, 1H), 7.65-7.54 (m, 2H), 6.97-6.78 (m, 3H), 6.29 (s, 1H), 6.18-6.15 (m, 1H), 6.03 (s, 2H), 4.32 (m, 2H), 3.99 (s, 3H), 3.87 (s, 3H).

[Example 8] Preparation of N-(2,4-dihydroxy-benzyl)-2,4-dimethoxy-5-(3,5-dimethyl-phenyl) Benzoic Acid Amide

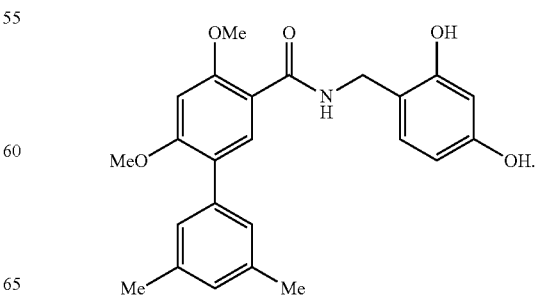

A method which was substantially same method used in Example 5 was used except for using 3,5-dimethylphenyl boronic acid (0.20 g) instead of 4-methoxy-benzene boronic acid (0.2 g, 1.3 mmol) so that the desired product was obtained as a white solid (0.1 g).

NMR results were confirmed as below. From the confirmation results as below, the white solid was confirmed as N-(2,4-dihydroxy-benzyl)-2,4-dimethoxy-5-(3,5-dimethyl-phenyl) benzoic acid amide.

$^1$H NMR (300 MHz, DMSO-$d_6$) 9.65 (s, 1H), 9.14 (s, 1H), 8.57 (brs, 1H), 7.80 (s, 1H), 7.00 (s, 2H), 6.95-6.93 (m, 2H), 6.79 (s, 1H), 6.28 (s, 1H), 6.18-6.15 (m, 1H), 4.33-4.31 (m, 2H), 4.00 (s, 3H), 3.86 (s, 3H), 2.29 (s, 6H).

[Example 9] Preparation of N-(2,4-dihydroxy-benzyl)-2,4-dimethoxy-5-(3,4-difluoro-phenyl) Benzoic Acid Amide

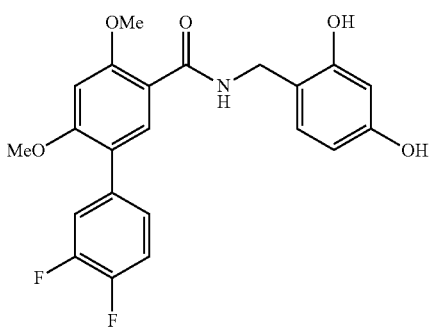

A method which was substantially same method used in Example 5 was used except for using 3,4-difluorophenyl boronic acid (0.20 g) instead of 4-methoxy-benzene boronic acid (0.2 g, 1.3 mmol) so that the desired product was obtained as a white solid (0.05 g).

NMR results were confirmed as below. From the confirmation results as below, the white solid was confirmed as N-(2,4-dihydroxy-benzyl)-2,4-dimethoxy-5-(3,4-difluoro-phenyl) benzoic acid amide.

$^1$H NMR (300 MHz, DMSO-$d_6$) 9.65 (s, 1H), 9.15 (s, 1H), 8.57 (brs, 1H), 7.84 (m, 1H), 7.49-7.47 (m, 2H), 7.27 (brs, 1H), 6.95-6.91 (m, 1H), 6.82 (s, 1H), 6.28 (s, 1H), 6.16 (s, 1H), 4.31 (m, 2H), 4.01 (s, 3H), 3.88 (s, 3H).

[Example 10] Preparation of N-(2,4-dihydroxy-benzyl)-2,4-dimethoxy-5-(3-nitro-phenyl) Benzoic Acid Amide

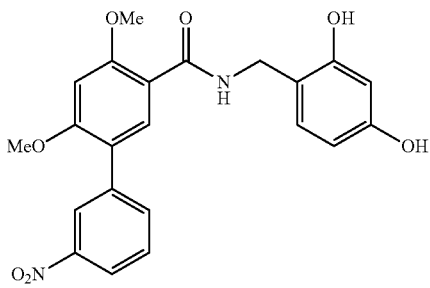 [SMILES: COc1cc(OC)c(-c2cccc([N+](=O)[O-])c2)cc1C(=O)NCc1ccc(O)cc1O]

A method which was substantially same method used in Example 5 was used except for using 3-nitrophenyl boronic acid (0.22 g) instead of 4-methoxy-benzene boronic acid (0.2 g, 1.3 mmol) so that the desired product was obtained as a solid (0.12 g).

NMR results were confirmed as below. From the confirmation results as below, the white solid was confirmed as N-(2,4-dihydroxy-benzyl)-2,4-dimethoxy-5-(3-nitro-phenyl) benzoic acid amide.

$^1$H NMR (300 MHz, DMSO-$d_6$) 9.62 (s, 1H), 9.17 (s, 1H), 8.55 (brs, 1H), 8.26-7.57 (m, 5H), 6.93-6.88 (m, 1H), 6.81 (m, 1H), 6.29 (s, 1H), 6.15 (m, 1H), 4.30 (m, 2H), 4.02 (s, 3H), 3.95 (s, 3H).

[Example 11] Preparation of 5-cyclohexene-1-yl-N-(2,4-dihydroxy-benzyl)-2,4-dimethoxy-benzoic Acid Amide

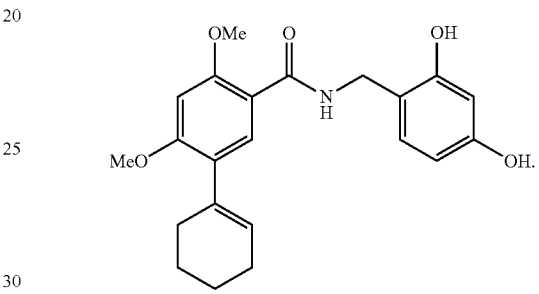

A method which was substantially same method used in Example 5 was used except for using 1-cyclohexene-1-yl-boronic acid pinacol ester (0.27 g) instead of 4-methoxy-benzene boronic acid (0.2 g, 1.3 mmol) so that the desired product was obtained as a solid (0.2 g).

NMR results were confirmed as below. From the confirmation results as below, the white solid was confirmed as 5-cyclohexene-1-yl-N-(2,4-dihydroxy-benzyl)-2,4-dimethoxy-benzoic acid amide.

$^1$H NMR (300 MHz, DMSO-$d_6$) 9.65 (s, 1H), 9.13 (s, 1H), 8.52 (brs, 1H), 7.64 (s, 1H), 6.94-6.90 (m, 1H), 6.66 (m, 1H), 6.27 (m, 1H), 6.17-6.15 (m, 1H), 5.63 (s, 1H), 4.29 (m, 2H), 3.95 (s, 3H), 3.88 (s, 3H), 2.23 (m, 2H), 2.11 (m, 2H), 1.61 (m, 4H).

[Example 12] Preparation of 5-cyclohexyl-N-(2,4-dihydroxy-benzyl)-2,4-dimethoxy-benzoic Acid Amide

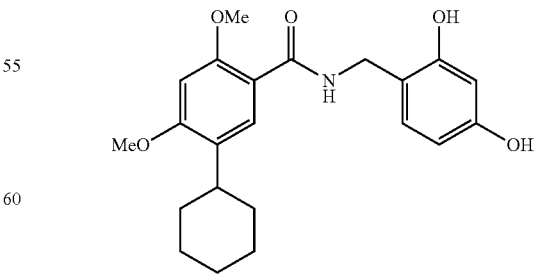

5-cyclohexene-1-yl-N-(2,4-dihydroxy-benzyl)-2,4-dimethoxy-benzoic acid amide (0.1 g) obtained in Example 11 was dissolved in ethanol (10 ml). Then 5% palladiumactivated carbon catalyst was put in the solution. Then the reduction reaction was performed for 4 hours under hydrogen pressure. The reaction mixture was filtered using Celite, and then was concentrated under reduced pressure, thereby obtaining the desired product (0.09 g) as a white solid.

NMR results were confirmed as below. From the confirmation results as below, the white solid was confirmed as 5-cyclohexyl-N-(2,4-dihydroxy-benzyl)-2,4-dimethoxy-benzoic acid amide.

$^1$H NMR (300 MHz, DMSO-$d_6$) 9.69 (s, 1H), 9.15 (s, 1H), 8.55 (brs, 1H), 7.76 (s, 1H), 6.96-6.94 (m, 1H), 6.29 (m, 1H), 6.19-6.16 (m, 1H), 4.31 (m, 2H), 3.95 (s, 3H), 3.89 (s, 3H), 2.79 (m, 1H), 1.80-1.65 (m, 5H), 1.40-1.10 (m, 5H).

[Experimental Example 1] Effect of Reducing Melanin Production in Melanocytes

The effect of inhibiting melanin production of the benzoic acid amide derivative compounds prepared in Examples in melanocytes was measured according to the Dooley's method. Mouse-derived B16F10 melanoma cells acquired from the Korean Cell Line Bank were used as cell lines. DMEM (Cat No. 11995), FBS (Cat No. 16000-044), and antibiotic-antifungal agents (Cat No. 15240-062) necessary for cell culturing were purchased from Invitrogen (GIBCO). The cell lines were cultured under the condition of 37° C. and 5% $CO_2$. The cultured B16F10 cells were detached using 0.05% trypsin-EDTA and inoculated onto a 48-well plate with the same cell number ($1 \times 10^4$ cells/well). From the next day, the culture medium was replaced with one containing 10 ppm of each compound of Examples for three consecutive days. Rucinol (Tokyo Chemical Industry (Japan, Cat. No. B3773)) exhibiting excellent whitening ingredient was used as a positive control. After 5 days, melanin was melted and extracted from the cells by treating with 1 N NaOH at 60° C. for 2 hours, which was quantitated by measuring absorbance at 405 nm. The concentrations ($IC_{50}$) of Examples required to inhibit melanin production in melanocytes to half were calculated and are given in the following Table 1.

TABLE 1

| Test material | $IC_{50}$ |
|---|---|
| Rucinol | $IC_{50}$ = 0.8 μM |
| Example 1 | $IC_{50}$ = 2.3 μM |
| Example 5 | $IC_{50}$ = 0.7 μM |
| Example 6 | $IC_{50}$ = 0.7 μM |
| Example 7 | $IC_{50}$ = 0.7 μM |
| Example 8 | $IC_{50}$ = 1.5 μM |
| Example 9 | $IC_{50}$ = 0.6 μM |
| Example 10 | $IC_{50}$ = 1.3 μM |
| Example 11 | $IC_{50}$ = 0.9 μM |
| Example 12 | $IC_{50}$ = 2.1 μM |

As seen from above, the compounds of Examples exhibit excellent inhibition ability of melanin production as rucinol. Accordingly, it can be seen that the benzoic acid amide derivative compounds according to the present invention have excellent skin whitening effect by reducing melanin production.

[Experimental Example 2] Effect of Inhibiting Mushroom Tyrosinase Activity

The effect of inhibiting mushroom tyrosinase activity of the benzoic acid amide derivative compounds of Examples was measured according to the method of Vanni, et al. Specifically, 49.5 μL of 0.1 M potassium phosphate buffer (pH 6.8), 45 μL of distilled water (DW), 0.5 μL (10 units) of mushroom tyrosinase (SIGMAT-7755), and 5 μL of each benzoic acid amide derivative compound of Examples were mixed and reacted at 37° C. for 10 minutes by mixing with 50 μL of 0.3 mg/mL tyrosine aqueous solution in a 96-well plate (total volume: 150 μL). Rucinol and 5-adamantane-1-yl-N-(2,4-dihydroxybenzyl)-2,4-dimethoxy-benzoic acid amide were used as a positive control. In particular, 5-adamantane-1-yl-N-(2,4-dihydroxy-benzyl)-2,4-dimethoxy-benzoic acid amide was a material synthesized by the present inventors, which was described in the US Patent Publication No.: US20140234241A1 which exhibits an excellent whitening effect thereof. Absorbance of the reaction solution was measured at 480 nm, and the concentrations of Examples required to inhibit tyrosinase activity to 50% ($IC_{50}$) were calculated and are given in the following Table 2.

TABLE 2

| Test material | $IC_{50}$ |
|---|---|
| Rucinol | 0.06 μM |
| 5-adamantane-1-yl-N-(2,4-dihydroxybenzyl)-2,4-dimethoxy-benzoic acid amide | 0.31 μM |
| Example 1 | 0.19 μM |
| Example 2 | 0.15 μM |
| Example 3 | 0.18 μM |
| Example 4 | 0.07 μM |
| Example 5 | 0.06 μM |
| Example 6 | 0.06 μM |
| Example 7 | 0.07 μM |
| Example 8 | 0.05 μM |
| Example 9 | 0.06 μM |
| Example 10 | 0.07 μM |
| Example 11 | 0.12 μM |
| Example 12 | 0.12 μM |

As seen from above, the benzoic acid amide derivative compounds of Examples have excellent effect of inhibiting mushroom tyrosinase activity. Their effects as inhibiting activity were equal to or more than rucinol and were superior compared to benzoic acid amide derivatives in which 5-adamantyl group was substituted, as described in US20140234241A1. Accordingly, it can be seen that the benzoic acid amide derivative compounds according to the present invention have excellent skin whitening effect by inhibiting tyrosinase activity.

Hereinafter, formulation examples of a composition comprising the compound, the isomer thereof, the pharmaceutically acceptable salt thereof, the prodrug thereof, the hydrate thereof, or the solvate thereof according to the present invention will be described in detail. However, the composition can be applied in various types of formulations. Thus, the following formulation examples are for illustrative purposes only, and the scope of the present invention is not limited thereby.

[Formulation Example 1] Cosmetic Water

A cosmetic water was prepared according to a commonly used method with the composition described in the following Table 3.

TABLE 3

| Ingredient | Content (wt %) |
|---|---|
| Example | 0.1 |
| Glycerin | 3.0 |
| Butylene glycol | 2.0 |

TABLE 3-continued

| Ingredient | Content (wt %) |
| --- | --- |
| Propylene glycol | 2.0 |
| Carboxyvinyl polymer | 0.1 |
| PEG 12 nonylphenyl ether | 0.2 |
| Polysorbate 80 | 0.4 |
| Ethanol | 10.0 |
| Triethanolamine | 0.1 |
| Antiseptic, pigment and flavor | Adequate |
| Purified water | Balance |

[Formulation Example 2] Nourishing Cream

A nourishing cream was prepared according to a commonly used method with the composition described in the following Table 4.

TABLE 4

| Ingredient | Content (wt %) |
| --- | --- |
| Example | 2.0 |
| Polysorbate 60 | 1.5 |
| Sorbitan sesquioleate | 0.5 |
| PEG 60 hydrogenated castor oil | 2.0 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Antiseptic, pigment and flavor | Adequate |
| Purified water | Balance |

[Formulation Example 3] Massage Cream

A massage cream is prepared according to a commonly employed method with the composition described in the following Table 5.

TABLE 5

| Ingredient | Content (wt %) |
| --- | --- |
| Example | 1.0 |
| Beeswax | 10.0 |
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Antiseptic, pigment and flavor | Adequate |
| Purified water | Balance |

[Formulation Example 4] Pack

A pack is prepared according to a commonly employed method with the composition described in the following Table 6.

TABLE 6

| Ingredient | Content (wt %) |
| --- | --- |
| Example | 0.2 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG 12 nonyl phenyl ether | 0.3 |
| Polysorbate 60 | 0.3 |
| Antiseptic, pigment and flavor | Adequate |
| Purified water | Balance |

[Formulation Example 5] Gel

A gel is prepared according to a commonly employed method with the composition described in the following Table 7.

TABLE 7

| Ingredient | Content (wt %) |
| --- | --- |
| Example | 0.5 |
| Sodium ethylenediaminetetraacetate | 0.05 |
| Glycerin | 5.0 |
| Carboxyvinyl polymer | 0.3 |
| Ethanol | 5.0 |
| PEG 60 hydrogenated castor oil | 0.5 |
| Triethanolamine | 0.3 |
| Antiseptic, pigment and flavor | Adequate |
| Purified water | Balance |

[Formulation Example 6] Ointment

An ointment is prepared according to a commonly employed method with the composition described in the following Table 8.

TABLE 8

| Ingredient | Content (wt %) |
| --- | --- |
| Example | 1.5 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Antiseptic, pigment and flavor | Adequate |
| Purified water | Balance |

[Formulation Example 7] Health Food

| Example | 1000 mg |
| --- | --- |
| Vitamin mixture | |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |

-continued

| | |
|---|---|
| Vitamin B12 | 0.2 μg |
| Vitamin C | 10 mg |
| Biotin | 10 μg |
| Nicotinamide | 1.7 mg |
| Folic acid | 50 μg |
| calcium pantothenate | 0.5 mg |
| Mineral mixture | |
| Ferrous sulfate | 1.75 mg |
| Zinc oxide | 0.82 mg |
| Magnesium carbonate | 25.3 mg |
| The first potassium phosphate | 15 mg |
| The second calcium phosphate | 55 mg |
| Potassium citrate | 90 mg |
| Calcium carbonate | 100 mg |
| Magnesium chloride | 24.8 mg |

The composition ratio of the mixture of vitamins and minerals is relatively suitable for mixing the components in a healthy foods as preferred formulation examples, but the mixing ratio may be modified optionally.

[Formulation Example 8] Health Beverage

| | |
|---|---|
| Example | 1000 mg |
| Citric acid | 1000 mg |
| Oligosaccharides | 100 g |
| Taurine | 1 g |
| Purified water | Balance |

The above ingredients were mixed according to a conventional method of preparing health beverage, and then heated and stirred at 85° C. for about 1 hour. Then the prepared solution was filtered and sterilized.

[Formulation Example 10] Tablet 100 mg of Example, 50 mg of soybean extract, 100 mg of glucose, 50 mg of red ginseng extract, 96 mg of starch, and 4 mg of magnesium stearate were mixed, and 40 mg of 30% ethanol was added to the mixture to form granules. Then granules were dried at 60° C. and pressed into tablets using a tablet press machine.

[Formulation Example 10] Granule 100 mg of Example, 50 mg of soybean extract, 100 mg of glucose, and 600 mg of starch were mixed, and 100 mg of 30% ethanol was added to the mixture to form granules. Then granules were dried at 60° C. to prepare granules and then were filled in bags.

The invention claimed is:

1. A compound of the following chemical formula 1, an isomer thereof, a pharmaceutically acceptable salt thereof, a hydrate thereof, or a solvate thereof:

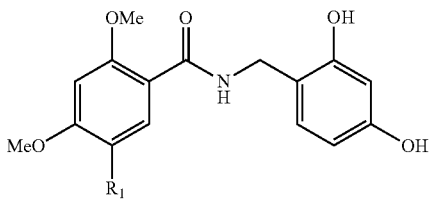

wherein $R_1$ of Chemical Formula 1 is selected from the group consisting of halogen, $C_1$-$C_5$ alkyl, $C_3$-$C_6$ cycloalkyl, $C_3$-$C_6$ cycloalkenyl, and $C_6$-$C_{18}$ aryl group, wherein the aryl group is unsubstituted or substituted with one or more selected from the group consisting of halogen, $C_1$-$C_5$ alkyl, $C_1$-$C_5$ alkoxy, methylenedioxy, and nitro groups.

2. The compound, the isomer thereof, the pharmaceutically acceptable salt thereof, the hydrate thereof, or the solvate thereof according to claim 1, wherein the compound is selected from the group consisting of N-(2,4-dihydroxy-benzyl)-2,4-dimethoxy-5-methyl-benzoic acid amide, 5-bromo-N-(2,4-dihydroxy-benzyl)-2,4-dimethoxy-benzoic acid amide, 5-tert-butyl-N-(2,4-dihydroxy-benzyl)-2,4-dimethoxy-benzoic acid amide, N-(2,4-dihydroxy-benzyl)-2,4-dimethoxy-5-phenyl-benzoic acid amide, N-(2,4-dihydroxy-benzyl)-2,4-dimethoxy-5-(4-fluoro-phenyl)-benzoic acid amide, N-(2,4-dihydroxy-benzyl)-2,4-dimethoxy-5-(4-methoxy-phenyl)-benzoic acid amide, 5-benzo[1,3]dioxol-5-yl-N-(2,4-dihydroxy-benzyl)-2,4-dimethoxy-benzoic acid amide, 5-cyclohexene-1-yl-N-(2,4-dihydroxy-benzyl)-2,4-dimethoxy-benzoic acid amide, N-(2,4-dihydroxy-benzyl)-2,4-dimethoxy-5-(3,5-dimethyl-phenyl)-benzoic acid amide, 5-cyclohexyl-N-(2,4-dihydroxy-benzyl)-2,4-dimethoxy-benzoic acid amide, N-(2,4-dihydroxy-benzyl)-2,4-dimethoxy-5-(3,4-difluoro-phenyl)-benzoic acid amide, and N-(2,4-dihydroxy-benzyl)-2,4-dimethoxy-5-(3-nitro-phenyl)-benzoic acid amide.

3. The compound, the isomer thereof, the pharmaceutically acceptable salt thereof, the hydrate thereof, or the solvate thereof according to claim 1, wherein the compound is N-(2,4-dihydroxy-benzyl)-2,4-dimethoxy-5-(3,5-dimethyl-phenyl)-benzoic acid amide.

4. A method of preparing the compound of chemical formula 1, the isomer thereof, the pharmaceutically acceptable salt thereof, the hydrate thereof, or the solvate thereof according to claim 1, wherein the method comprises a first step of reacting a benzoic acid derivative of the following chemical formula 2 and a hydroxyl group substituted alkyl-phenyl amine as reactants:

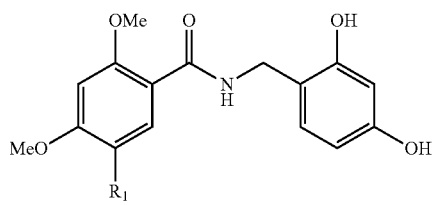

wherein $R_1$ of chemical formula 1 is selected from the group consisting of halogen, $C_1$-$C_5$ alkyl, $C_3$-$C_6$ cycloalkyl, $C_3$-$C_6$ cycloalkenyl and $C_6$-$C_{18}$ aryl group, wherein the aryl group is unsubstituted or substituted with one or more selected from the group consisting of halogen, $C_1$-$C_5$ alkyl, $C_1$-$C_5$ alkoxy, methylenedioxy, and nitro groups; and

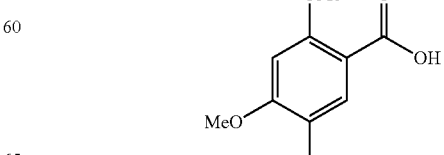

wherein R of chemical formula 2 is selected from the group consisting of halogen, $C_1$-$C_5$ alkyl, $C_3$-$C_6$ cycloalkyl, and $C_3$-$C_6$ cycloalkenyl; wherein the first step is performed in presence of N-hydroxysuccinimide and N,N'-dicyclohexylcarbodiimide (DCC).

5. The method of preparing the compound of chemical formula 1 according to claim 4, wherein the R of chemical formula 2 is halogen.

6. The method of preparing the compound of chemical formula 1 according to claim 5, wherein the method further comprises a second step of reacting the resulting bromo benzoic acid amide derivative and arylboronic acid, in a case where the R of chemical formula 2 is bromine group to form a bromo benzoic acid derivative.

7. The method of preparing the compound of chemical formula 1 according to claim 6, wherein the second step is performed in presence of a palladium catalyst under base condition.

8. The method of preparing the compound of chemical formula 1 according to claim 6, wherein the aryl bromic acid is unsubstituted or substituted with one or more selected from the group consisting of halogen, $C_1$-$C_5$ alkyl, $C_1$-$C_5$ alkoxy, methylenedioxy, and nitro groups.

9. A method for skin whitening comprising administering the compound according to claim 1, the isomer thereof, the pharmaceutically acceptable salt thereof, the hydrate thereof, or the solvate thereof to a subject in need thereof.

10. The method for skin whitening according to claim 9, wherein the compound, the isomer thereof, the pharmaceutically acceptable salt thereof, the hydrate thereof, or the solvate thereof is contained in a composition in a concentration of 0.01 wt % to 20 wt % based on total weight of the composition.

11. The method for skin whitening according to claim 9, wherein the compound, the isomer thereof, the pharmaceutically acceptable salt thereof, the hydrate thereof, or the solvate thereof inhibits melanin production.

12. The method for skin whitening according to claim 9, wherein the compound, the isomer thereof, the pharmaceutically acceptable salt thereof, the hydrate thereof, or the solvate thereof inhibits tyrosinase activity.

13. The method according to claim 9, wherein the compound, the isomer thereof, the pharmaceutically acceptable salt thereof, the hydrate thereof, or the solvate thereof is one for external application to skin.

14. The method according to claim 9, wherein the compound, the isomer thereof, the pharmaceutically acceptable salt thereof, the hydrate thereof, or the solvate thereof is one for a cosmetic composition, a pharmaceutical composition, or health food composition.

* * * * *